United States Patent [19]

Kretzschmar et al.

[11] Patent Number: 5,096,905

[45] Date of Patent: Mar. 17, 1992

[54] BASIC CLEAVAGE PRODUCTS OF ELAIOPHYLIN AND ELAIOPHYLIN DERIVATIVES AND USE THEREOF

[75] Inventors: Gerhard Kretzschmar, Eschborn; Peter Hammann, Keikheim; Dieter Düwel, Hofheim am Taunus; Gerhard Wöhner, Wunstorf; Rüdiger Marquardt, Frankfurt am Main; Klaus Kühlein, Kelkheim, all of Fed. Rep. of Germany

[73] Assignee: Hoechst Aktiengesellschaft, Frankfurt am Main, Fed. Rep. of Germany

[21] Appl. No.: 407,301

[22] Filed: Sep. 14, 1989

[30] Foreign Application Priority Data

Sep. 16, 1988 [DE] Fed. Rep. of Germany ....... 3831465

[51] Int. Cl.$^5$ .................... A61K 31/50; C07D 493/10
[52] U.S. Cl. .................... 514/252; 514/256; 514/275; 514/336; 514/352; 514/444; 514/447; 514/460; 544/295; 544/323; 544/336; 544/357; 546/251; 546/255; 546/256; 549/60; 549/68; 549/343; 549/415
[58] Field of Search .................... 549/343, 415, 60, 68; 514/460, 252, 256, 275, 336, 352, 444, 447; 544/295, 323, 336, 357; 546/251, 255, 256

[56] References Cited

U.S. PATENT DOCUMENTS

| 4,027,034 | 5/1977 | Messersmith | 514/460 |
| 4,359,583 | 11/1982 | Mizutani et al. | 549/343 |
| 4,625,041 | 11/1986 | Celmer et al. | 549/343 |
| 4,804,680 | 2/1989 | Goudie et al. | 549/343 |

FOREIGN PATENT DOCUMENTS

| 3402075 | 8/1985 | Fed. Rep. of Germany . |
| 60-190785 | 9/1985 | Japan . |
| 61-36295 | 2/1986 | Japan . |

OTHER PUBLICATIONS

N. Janes, "Recent Advances in the Chemistry of Insect Control", Special Publication No. 53, 1984, pp. xi-xii.
G. Werner et al., "Metabolic Products of Microorganisms", J. of Antibiotics 1984, vol. 37, No. 2, pp. 110-117.
M. Arai, "Azalomycine B and F, Two New Antibiotics", J. of Antibiotics, 1960, vol. 13, No. 1, pp. 46-50.
F. Arcamone et al., "Melanosporin and Elaiphylin, New Antibiotics from Streptomyces Melanosporus", Giorn. Microbiol., 1959, vol. 7, pp. 207-216.
H. Kaiser et al., "Stoffwechselprodukte von Mikroorganismen", Helvetica Chimica Acta, 1981, vol. 64, Fasc. 2, No. 41, pp. 407-424.
S. Ley et al., "A Conformational Study of Elaiophylin by X-Ray Crystallography and Difference $^1$H NMR Methods ... ", Tetrahedron Letters, 1982, vol. 23, No. 11, pp. 1207-1210.
M. Sutter et al., "Synthese von (2E,4E,6S,7R,10E,12E,14S,15R)-6,7,14,15-Tetramethyl-8,16-Dioxa-2,4,10,12-Cyclohexadecatetraen-1,9-Dion.-Ein Modellsystem fur Elaiophylin", Liebigs Ann. Chem., 1983, pp. 939-949.
T. Wakamatsu et al., "Enantioselective Synthesis of 16-Membered a, b, q, w-Unsaturated Diolide ... ", Heterocycles, 1987, vol. 25, pp. 43-46.
D. Seebach et al., "Total Synthesis of (+)-11,11'-Di--O-Methylelaiophylidene: An Aglycone of Elaiophylin", J. Am. Chem. Soc., 1985, vol. 107, pp. 5292-5293.
K. Toshima et al., "Total Synthesis of Elaiophylin", Tetrahedron Letters, 1986, vol. 27, No. 39, pp. 4741-4744.
D. Seebach et al., "(+)-11, 11'-Di-O-Methylelaiophylidene—Preparation from Elaiophylin and Total Synthesis from (R)-3-Hydroxybutyrate and (S)-Malate" Liebigs Ann. Chem , 1986, pp. 1281-1308.

OTHER DOCUMENTS

Chemical Abstract No. 104:109317a, March 1986.
Chemical Abstract No. 107:78160z, August 1987.
Chemical Abstract No. 110:75912x, February 1989.
Chemical Abstract No. 103:123227g, October 1985.

*Primary Examiner*—C. Warren Ivy
*Assistant Examiner*—Ba K. Trinh
*Attorney, Agent, or Firm*—Finnegan, Henderson, Farabow, Garrett, and Dunner

[57] ABSTRACT

The invention relates to elaiophylin derivatives of the formulae (I), (I'), (III) and (III')

(Abstract continued on next page.)

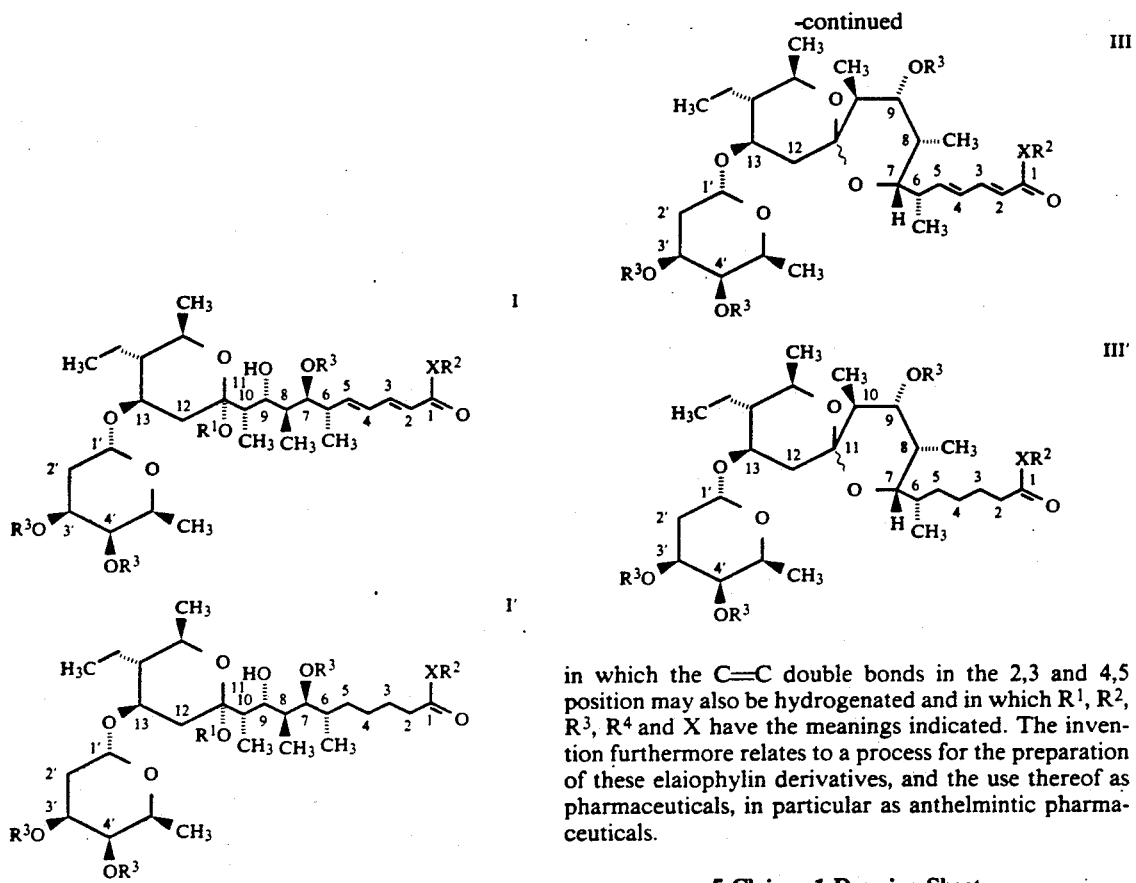
in which the C=C double bonds in the 2,3 and 4,5 position may also be hydrogenated and in which $R^1$, $R^2$, $R^3$, $R^4$ and X have the meanings indicated. The invention furthermore relates to a process for the preparation of these elaiophylin derivatives, and the use thereof as pharmaceuticals, in particular as anthelmintic pharmaceuticals.
5 Claims, 1 Drawing Sheet

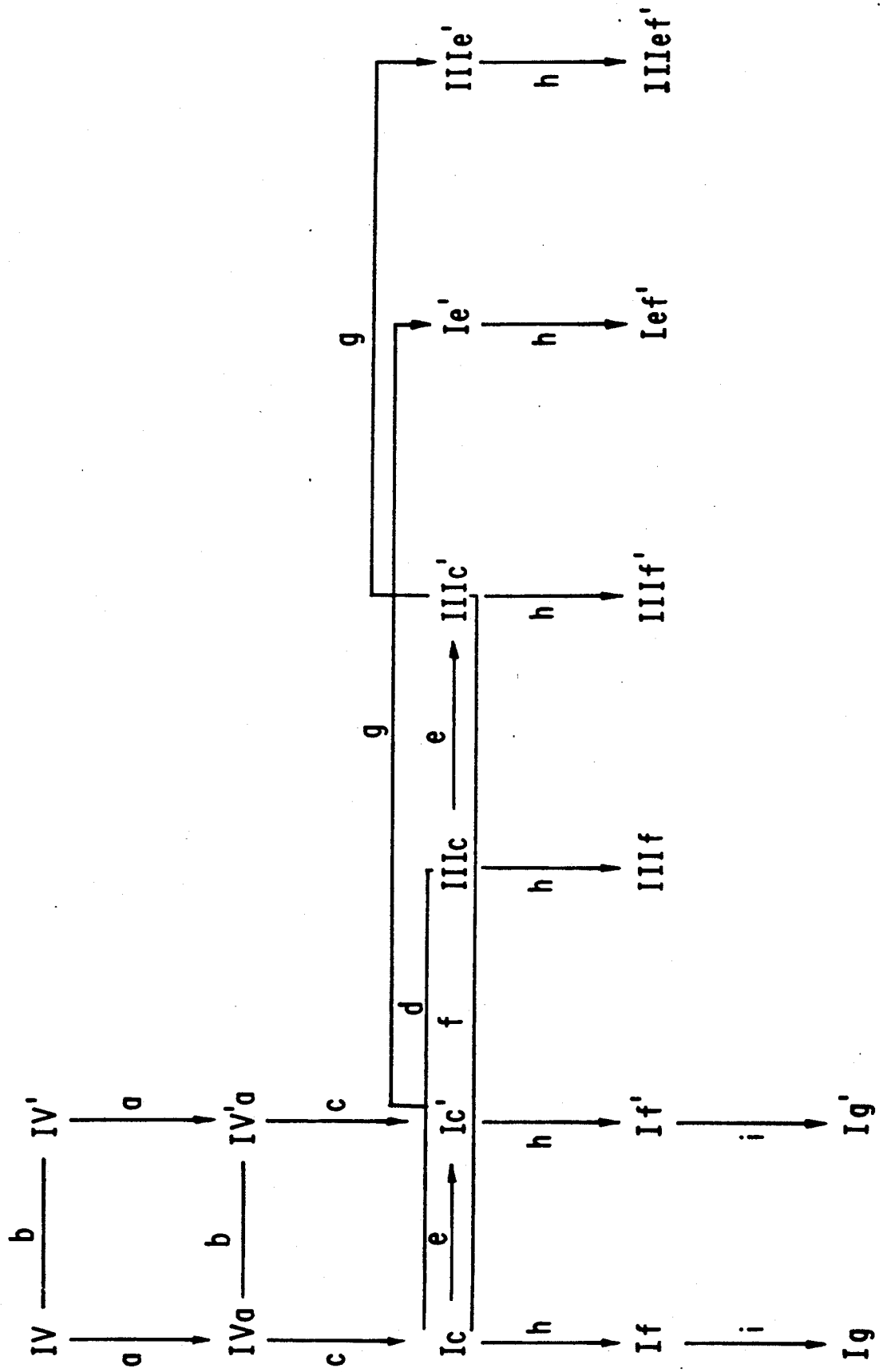

BASIC CLEAVAGE PRODUCTS OF ELAIOPHYLIN AND ELAIOPHYLIN DERIVATIVES AND USE THEREOF

Macrocycles having a 16-membered lactone structure are of particular industrial interest as anthelmintic acitve substances. Known representatives of this class of active substances are the avermectins and milbemycins (review in: Spec. Publ.—R. Soc. Chem. 53, Recent Advances Chem. Insect Control, 1985) and the bafilomycins (G. Werner et al., J. Antibiot. 37, 110 (1984)), tubamycin (DE 3,402,075 Al) and leucanicidin (HP 60-190,785).

The macrolide antibiotic elaiophylin was isolated for the first time by Arcamone et al. 1959 (Giorn. Microbiol 7, 207, 1959) from cultures of Streptomyces melanosporus and later described under the name azalomycin B by Arai (J. Antibiot., Ser. A, 13, 45, 51 (1960)).

A greatly improved process for the preparation of elaiophylin and its use as an anthelmintic is proposed in German Patent Application P 37 21 711.4.

The structure of elaiophylin was unambiguously assigned by means of spectroscopic investigations and degradation reactions by kaiser et al. (Helv. Chim. Acta, 64 (1981), 407) and also by X-ray diffraction (S. V. Ley et al., Tetrahedron Lett., 1207 (1982)).

The interesting biological properties and the unusual $C_2$ symmetry of this 16-membered macrodiolide compound also stimulated synthetic investigations on he enantioselective degradation of the macrocycle as a model structure (D. Seebach et al., Leibigs Ann. Chem. 1983, 939 and T. Wakamatsu et al., Heterocycles 25, 43, 1987). These investigations finally led to the total synthesis of the aglycone 11,11'-di-O-methylelaiophylidene (D. Seebach et al., J. Am Chem. Soc., 107, 4292, 1985) the naturally identical compound by m. Kinoshita et al (Tetrahedron Lett. 1986, 4741).

Whereas elaiophylin can be degraded in a defined manner via the isolatable aglycone by treatment with acids, the reaction with mild bases leads to the complete, uncontrolled decomposition of the molecule (D. Seebach et al., Liebigs, Ann. Chem. 1281, 1986).

However, if an in situ derivatization of the elaiophylin or of elaiophylin derivatives to give the 11,11'-di-O-alkyl derivatives is first carried out and the product is then reacted with alcoholates, the secondary elaiophylin ester derived from the symmetrical macrodiolide structure is obtained in high yield. The 11,11'-O-alkyl derivatives have already been described in Janapense Offenlegungsschrift 61-36,295 (Yokura et al.). An improved process for their preparation by means of metal salt catalysis is proposed in German Patent Application P 37 36 960.1.

It has now surprisingly been found that not only the macrocycle elaiophylin itself can be used as an anthelmintic, but that also the identical seco-halves of the natural substance and its derivatives prepared for the first time by basic degradation have an anthelmintic activity which is comparable to that of elaiophylin itself.

The invention relates to:
1. elaiophylin derivatives of the formulae (I) and (III)

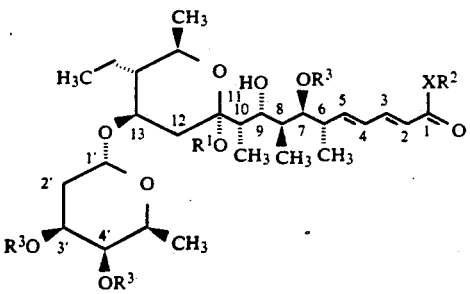

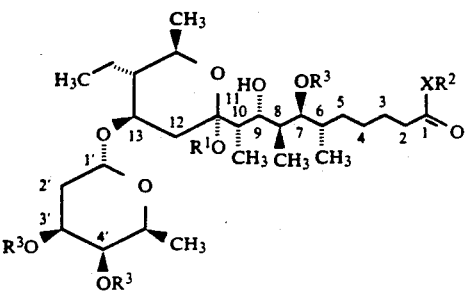

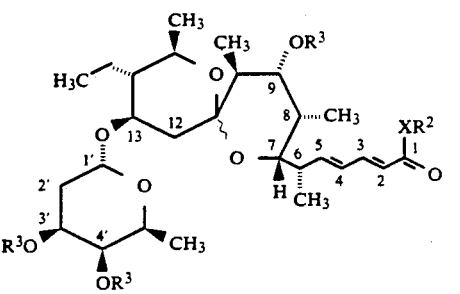

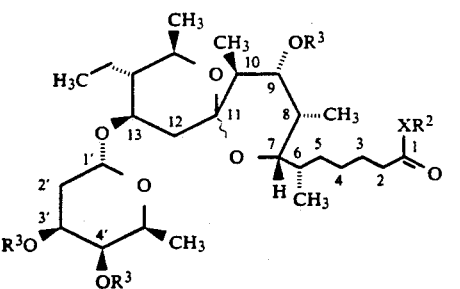

in which the C=C double bonds in the 2,3 and 4,5 position may also be hydrogenated (formulae (I') and (III')) and in which $R^1$ denotes hydrogen or a radical of the formula (VI)

$$-(CH_2)_n-R^4 \qquad (VI)$$

in which
n=1 to 3 and
$R^4$ is hydrogen, $C_1-C_{15}$-alkyl, $C_2-C_{15}$-alkenyl, $C_2-C_{15}$-alkynyl, $C_3-C_9$-cycloalkyl, phenyl or a heteroaryl having 3 to 9 ring atoms, where the heterocycle is optionally substituted by chlorine, bromine, iodine, nitro, hydroxyl or $C_1-C_4$-alkyl or $C_1-C_4$-alkoxy, X is O or, if $R^1$ is not hydrogen and the C=C double bonds in formula (I) and (III) are hydrogenated in the b 2,3 and 4,5 position, is also NH, $R^2$ is hydrogen or $C_1-C_4$-alkyl or, if X is NH, is a radical having the formula VI, where n and $R^4$ have the abovementioned meanings and $R^3$ is hydrogen or a radical of the formula (II)

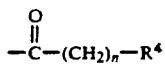
(II)

in which n and $R^4$ have the abovementioned meanings.

The invention furthermore relates to a process for the preparation of elaiophylin derivatives of the formulae I, III, I' and III' which comprises (a) reacting elaiophylin of the fomrula (IV), in whic $R^1$, $R^2$ and $R^3$ are hydrogen, with an alcohol of the formula HO—$(CH_2)_n$—$R^4$, in which n and $R^4$ have the meanings indicated above for formula (IV), to give a compound of the formula (IVa) in which $R^1$ is $(CH_2)_n$—$R^4$, where n and $R^4$ have the meanings indicated above for formula (VI) and (b) either first reducing the intermediate (IVa), optionally after its isolation, in the presence of hydrogenation catalysts to give the compound (IVa'), in which the C=C double bonds in position 2,3 and 4,5 and also 2',3' and 4',5' are hydrogenated and $R^1$ is unchanged compared to the compound of the formula (IVa), or (c) reacting the intermediate (IVa) obtainable by reaction (a) or the intermediate (IVa') obtainable by reaction (b) with alkali metal alcoholates of the formula $R^2O^-M^=$, in which M is lithium, sodium or potassium and $R^2$ has the meaning indicated above for formula (VI), to give compounds of the formula (Ic) or (Ic'), in which $R^3$ is hydrogen, $XR^2$ is a radical $OR^2$ and $R^1$ and $R^2$ have the meanings indicated above for formula (VI) in addition to hydrogen, or (d) reacting a compound of the formula (Ic) with a Lewis acid in a non-aqueous solvent, to give a compound of the formula (IIIc), in which the meaning of $XR^2$ and $R^3$ remains unchanged compared to the starting compound of the formula (Ic), or (e) reducing a compound of the formula (Ic) or (IIIc) with hydrogen in the presence of hydrogenation catalysts to give compounds of the formulae (Ic') or (IIIc'), in which $R^1$, $XR^2$ and $R^3$ remain unchanged compared to the compound of the formulae (Ic) or (IIIc), or (f) reducing a compound of the formula (Ic) with hydrogenation catalysts which additionally exhibit Lewis acid activity to give a compound of the formula (IIIc'), or (g) reacting a compound of the formula (Ic') or (IIIc') with ammonia or a primary amine of the formula $H_2N$—$(CH_{2n})$—$R^4$, in which n and $R^4$ have the meainings indicated above for formula (VI), to give compounds of the formula (Ie') or (IIIe'), in which X is NH, or (h) reacting a compound of the formulae (Ic), (Ic'), (IIIc), (IIIc'), (Ie') or (IIIe') with a compound of the formula (V)

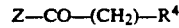
(V)

in which n and $R^4$ have the meanings indicated for formula (II) and in which Z is a nucleofungic group, to give a compound of the formulae (I) or (III) or (I') or (III'), in which $R^1$, $XR^2$ and $R^3$ have the meanings indicated above for the formulae (I), (I'), (III) and (III'), or (i) reacting a compound of the formula (I) or (I'), in which $R^1$ and $R^3$ have the meanings indicated above other than hydrogen and also $R^3$ has the meanings indicated above for formula (VI), with lewis acid in the presence of an aqueous solvent, a compound of the formula (I) or (I') being obtained, in which $R^1$ is hydrogen and $XR^2$ and $R^3$ remain unchanged compared to the starting compound (I) or (I') for the reaction i).

The invention additionally relates to the elaiophylin derivatives as defined above, for use as pharmaceuticals, in particular as anthelmintic pharmaceuticals.

BRIEF DESCRIPTION OF THE DRAWING

The single FIGURE is a flow diagram of a reaction in accordance with the present invention.

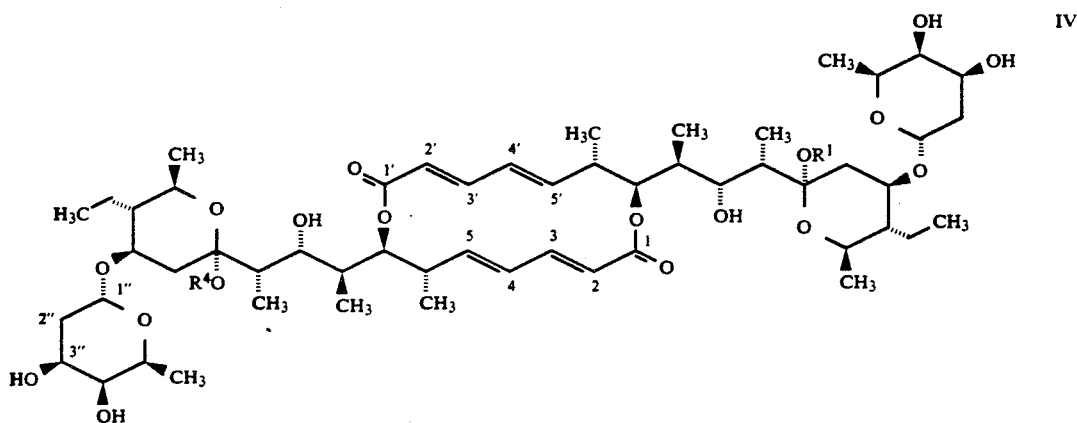

-continued

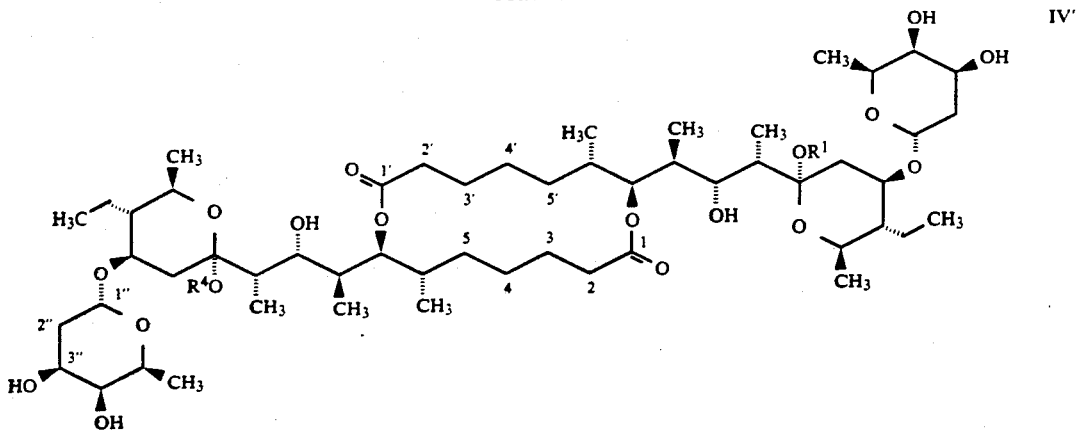

| Compound | General formula | $R^1$ | X | $R^2$ | $R^3$ |
|---|---|---|---|---|---|
| IV | IV | H | — | — | — |
| IV' | IV' | H | — | — | — |
| IVa | IV | R | — | — | — |
| IVa' | IV' | R | — | — | — |
| Ic | I | R | O | R | H |
| Ic' | I' | R | O | R | H |
| IIIc | III | — | O | R | H |
| IIIc' | III' | — | O | R | H |
| Ie' | I' | R | NH | R or H | H |
| IIIe' | III' | — | NH | R or H | H |
| If | I | R | O | R | CO—R |
| If' | I' | R | O | R | CO—R |
| IIIf | III | — | O | R | CO—R |
| IIIf' | III' | — | O | R | CO—R |
| Ief' | I' | R | NH | R or H | CO—R |
| IIIef' | III' | — | NH | R or H | CO—R |
| Ig | I | H | O | R | CO—R |
| Ig' | I' | H | O | R | CO—R |

R is $(CH_2)_n$—$R^4$, where n is an integer of 1 to 3 and $R^4$ represents hydrogen, $C_1$-$C_{15}$-alkyl, $C_2$-$C_{15}$-alkenyl, $C_2$-$C_{15}$-alkynyl, $C_3$-$C_9$-cycloalkyl, phenyl or a heteroaryl having 3 to 9 ring atoms, where the heterocycle is optionally substituted by chlorine, bromine, iodine, nitro, hydroxyl or $C_1$-$C_4$-alkyl or $C_1$-$C_4$-alkoxy.

In the hydrogenation processes (b) and (e), it should be borne in mind that functional groups which can be reduced with hydrogen in the radicals $R^1$, $XR^2$ and $R^3$ of the unsaturated compound of the general formulae (I), (III) and (IV) to be hydrogenated in each case may at the same time additionally be reduced, which may possibly make necessary a change in he sequence of the process steps if this hydrogenation is not desired in the side chain. Thus, for example, the radicals $R^1$, if they simultaneously possess functional groups which can be hydrogenated, are also introduced by means of process (a) only after carrying out process steps (b) and (c) and hydrogenatable radicals $R^3$ are expediently introduced by means of process (h) only after process step (e). Analogous considerations also apply if $R^1$ or $R^3$ carry functional groups poisoning the hydrogenation catalyst, such as, for example, in sulfur compounds.

Heteroaryl is to be understood as meaning heteroaromatic hydrocarbons, in particular thiophene and furan, but also pyridine, pyrimidine and pyrazine. The C-1- to C-10 side chains of the compounds of the formula (I) may—depending on the type of the substituents $R^1$ and $R^3$—be hydrogenated or unhydrogenated. This also applies to the radical $XR^2$, if X is oxygen. If X=NH, the compounds of the formulae (I) and (II) are present in the hydrogenated form.

In the following the processes (a) to (i), which make it possible to prepare the differently substituted compounds of the formulae (I) and (III), are described in more detail.

The substituent $R^1$ in elaiophylin (IV, $R^1$=H) or in 2,2',3,3',3,4,4',5,5'-octahydroelaiophylin (IV, $R^1$=H, C=C double bonds hydrogenated, for example by process (b)) can be introduced with he aid of process (a). This is expedient for carrying out the cleavage reaction by process (c), since elaiophylin and elaiophylin derivatives of the formula (IV), in which $R^1$ is hydrogen, can be decomposed in an uncontrollable manner using strong bases such as hydroxyl ions, metal alcoholates or amines. In the process according to the invention, a procedure is best used in which the starting compounds mentioned are reacted with an excess of up to 50-fold of an alcohol of the formula HO—$(CH_2)_n$—$R^4$, if necessary in the presence of catalytic amounts of a Lewis acid, until completion of the reaction.

A variant of the process consists in working in a suitable solvent such as chloroform, methylene chloride, THF, ethyl acetate or dioxane. Suitable Lewis acids are, for example, halides of copper, iron or lithium, in particular $CuCl_2$, $FeCl_3$ or LiBr.

The concentration of the Lewis acid—relative to elaiophylin or the elaiophylin derivative—is 0.1 to 5 % by weight, preferably 0.5 to 1 % by weight. The reaction temperatures in this case are between −40° C. and +100° C., in particular between 0° C. and 30° C., preferably using a solvent between the solidification point and the boiling point of the solvent, in particular between 0° C. and 30° C. The reaction times are 1 to 180 minutes, preferably 5 to 60 minutes. The completion of the reaction can be determined, for example, by means of thin layer chromatography.

The elaiophylin required as a starting substance can be prepared, for example, according to the process proposed in German Patent Application P 37 21 722.4. Here, elaiophylin is produced as a fermentation product of cultures of the strain Streptomyces violaceoniger DSM 4137 or Streptomyces parvulus DSM 3816.

In order to isolate elaiophylin, culture medium and mycelium, preferably only the mycelium, are extracted using organic solvents, such as chloroform or ethyl acetate, preferably ethyl acetate.

Isolation in a pures state is carried out by crystallization from the organic solvent, preferably from ethyl acetate.

The 2,2',3,3',4,4',5,5'-octahydroelaiophylin required as a starting substance can be prepared from this by the literature process of Kaiser et al. (Helv. Chim. Acta, 64 (1981). 407).

The C=C double bonds of the macrodiolide ring can be hydrogenated with the aid of process variant (b). If the desired elaiophylin derivative is intended to contain unsaturated or reducible substituents $R^1$, the hydrogenation of the macrodiolide ring is expediently carried out before the coupling of the corresponding unsaturated substituents by process (a).

In process variant (b), a procedure is best used in which the elaiophylin or elaiophylin derivative to be hydrogenated, preferably dissolved in a solvent such as methanol, ethanol, isopropanol or ethyl acetate or a mixture of these solvents in the presence of a standard hydrogenation catalyst, is reacted with hydrogen according to processes known from the literature. Standard hydrogenation catalysts are, for example, elements of the 8th group such as platinum, palladium or alternatively nickel, which are usually applied, for example, to active carbon, silica or alumina supports for the purpose of enlarging the reactive surface area. If the reaction is carried out in an absolute primary alcohol as a solvent, a ketalization to give the $C_{11}/C_{11}'$-di-O-alkylene is obtained in addition to a hydrogenation of the C=C double bonds using specific catalysts (see Example 2).

Depending on the catalyst used, the reaction can be carried out both with and without hydrogen overpressure, for example up to 1 atmosphere. The reaction temperatures are between 0° C. and 40° C., preferably room temperature. The reaction times are dependent on the batch size and the concentration of the compound to be reduced. Such hydrogenation processes are described, for example, in Organikum, Organisch-Chemisches Grundpraktikum (Basic Practice of Organic Chemistry), 15th edition, VEB Deutscher Verlag der Wissenschaften, Berlin, 1976, p. 359-371.

The elaiophylin derivative prepared according to processes (a) or (b) is split by double transesterification of the macrodiolide ring by means of alcoholates into the two identical seco-elaiophylin esters with the aid of process (c). In this case, a procedure is best used in which the elaiophylin derivative is reacted with a 1.1- to 5-fold excess of the alcoholate $R^2O^-M^+$ concerned in the alcohol $R^2OH$ as a solvent until completion of the reaction. Solvent mixtures of the alcohol $R^2OH$ and a suitable inert solvent such as dichloromethane, tetrahydrofuran or dioxane are also suitable. The concentration of alcoholate $R^2O^-M^+$ can be varied in the range from 0.1-3.0 mol/l of solvent, preferably the reaction is carried out using a concentration of 0.8 to 1.2 mol/l. The reaction temperatures in this case are between $-30°$ C. and $+30°$ C. The reaction times are 10 minutes to 6 hours, preferably 30 minutes to 2 hours. The completion of the reaction can be determined, for example, by means of thin layer chromatography on silica gel using solvent mixtures of dichloromethane and ethanol. If the radical $R^1$ introduced with the aid of process (a) corresponds to the radical $R^2$ of the alcoholate $R^2O^-M^+$, processes (a) and (c) can be carried out in a one-pot process without isolation of the intermediates obtained by process (a). In this case, the calculated amount of the alcoholate $R^2O^-M^+$ (0.1-3.0 mol/l) is added directly to the product solution obtained by process (a) so that the desired alcoholate concentration is achieved and the procedure is then as described above.

The C=C double bond of the seco-elaiophylin derivatives (I and III) can be hydrogenated with the aid of process variants (e) and (f), it basically being possible to work analogously to process (b) and either products of the general formulae (I) or (III) resulting from compounds (I), depending on the catalyst activity and radical $R^3$. Seco-elaiophylin derivatives of the general formula (I), in which the two C=C double bonds of the aliphatic side chain are intact and which have been acylated according to process (h), can only yield hydrogenated seco-elaiophylin erivatives of the type (I), all standard hydrogenation catalysts embodied under process variant (b) being suitable. On the other hand, the corresponding unsaturated derivatives of the formula (I) in which $R^3$ is hydrogen react with specific hydrogenation catalysts with the elimination of $R^1OH$ to give the products (III) hydrogenated in the side chain. An example of one such "specific hydrogenation catalyst" is the catalyst 10 percent palladium on carbon from the firm Merck. In comparison, the hydrogenated derivatives of the formula (I) are obtained from the unsaturated derivatives of the formula (I) in which $R^3$ is hydrogen, for exmaple using the hydrogenation catalyst 10 percent palladium on charcoal from the firm Riedel-de-Häen. The products (III) are formed as a stereoisomer mixture relative to the new asymmetric center on C-11.

Process (g) allows the conversion of the hydrogenated seco-elaiophylin estes of the formulae (I) and (III), in which X is oxygen, $R^1$ is H and $R^3$ is hydrogen, into the seco-elaiophylin acid amides by replacement of $-OR^2$ with $-NH_2$ or $NHR^2$. In this case, a procedure is best used in which the seco-elaiophylin ester concerned is reacted in equimolar amounts or in an excess of up to 100-fold with the amine $H_2N-(CH_2)_n-R^4$ or $NH_3$ dissolved in solvents such as methanol, ethanol, isopropanol, ethyl acetate, tetrahydrofuran or dioxane, until completion of the reaction. A variant consists in employing the amine itself as a solvent.

The reaction temperatures in this case are between 20° C. and 100° C., preferably using a solvent between the solidification point and the boiling point of the solvent, in particular between 20° C. and 60° C. The reaction times are 1-72 hours, preferably 8-48 hours. The completion of the reaction can be determined, for example, by means of TLC checking.

Amines of the formula $H_2NR$ are either commercially available or easy to prepare by standard methods of organic synthesis.

The hydroxyl groups in the 3'- and 4'-position of the seco-elaiphylin derivatives (I) and (III) can be esterified with the aid of process variant (h). If the reaction starts here from a compound of the formula (I) in which $R^3$ in hydrogen, the hydroxyl group in the 7-position is additionally selectively esterified, while if it starts from a compound of the formula (III) in which $R^3$ is hydrogen, the hydroxyl group in the 9-position is additionally esterified. Since in a compound of the formula (I) only the hydroxyl group in the 7-position is additionally esterified and the hydroxyl group in the 9-position is retained, it can be concluded from the experimental findings that a triacyl derivative according to process variants (d) and (e) can only be reacted further to give a product of the structure type (I), since the possibility of cyclization of derivatives of the structure type (III) is blocked. In process variant (h), a procedure is best used in which the seco-elaiophylin derivative of the formula (I) or (III), in which $R^3$ is hydrogen, is reacted in equimolar amounts or in an excess of up to 50-fold, if appropriate in an inert, aprotic solvent such as chloroform, methylene chloride, tetrahydrofuran (THF), ethyl acetate or dioxane, with a compound of the formula (V) or (V') until completion of the reaction, if appropriate in the presence of a base, preferably pyridine. The addition of an acylation catalyst such as, for example, 4-dimethylaminopyridine (DMAP) is necessary with reaction-supporting reagents of the formula (V) or (V').

Suitable nucleofugic groups are chloride, bromide, imidazolide or acid anhydrides.

The reaction temperature in this case are between $-70°$ C. and $+100°$ C., preferably using a solvent between the solidification point and the boiling point of the solvent, in particular between $-70°$ C. and $+40°$ C. The reaction times are 1 to 180 hours, preferably 1 to 48 hours, particularly preferably 1 to 8 hours. The completion of the reaction can be determined, for example, by means of thin layer chromatography (TLC checking).

If not commercially available, the starting compounds for the process variant (h), which are compounds of the formula (V) and/or (V'), can be prepared in a simple manner by methods known from the literature. For example, the acid chlorides (X=U) are obtained by reaction of the corresponding carboxylic acid with thionyl chloride, $PCl_3$ or $PCl_5$. Such processes are described, for example, in Gattermann/Wieland, "Die Praxis des Organischen Chemikers" (The Practice of the Organic Chemist), 43rd edition, Walter de Gruyter, Berlin, New York 1982, p. 303 ff.

It is possible with the aid of process (i) to split off again the protective group $R^1$ in the seco-elaiophylin derivatives of the formula (I) introduced into elaiophylin in process step (a) and to replace it by hydrogen.

A procedure is used here in which the corresponding seco-elaiophylin derivative of the formula (I), in which $R^1$ is not hydrogen, is dissolved with a Lewis acid in an aqueous secondary or tertiary alcohol and reacted until completion of the reaction. The concentration of the Lewis acid—relative to the seco-elaiophylin derivative—is 0.1–5% by weight, preferably 0.5–1% by weight. Suitable solvents are, for exmaple, isopropanol, 2-butanol or tert-butanol, preferably isopropanol, and the water content is 0.5–10% by weight, preferably 0.5–2% by weight. The reaction temperatures in this case are between $-20°$ C. and room temperature and the reaction times are 5–60 minutes.

Suitable Lewis acids are the metal salts already mentioned in process (a), in particular $FeCl_3$.

Compounds of the general formula (I) in which $R^3$ is hydrogen and in which the two C=C double bonds may also be hydrogenated can be converted into the spiro compounds (III) with the aid of process variant (d). In this case, a process entirely analogous to process (i) is used, with the exception that the compound of the formula (I) concerned is reacted in an anhydrous solvent. Suitable solvents are, for example, dichloromethane, THF, dioxane, ethyl acetate or alcohols such as methanol, ethanol, propanol or isopropanol, preferably methanol or ethanol.

Suitable Lewis acids are the metal salts already mentioned in processes (a) and (i), preferably $FeCl_3$. The concentration of the Lewis acid, the reaction temperature and the reaction time are analogous to those described in process (i).

The purification, isolation and working up of the substances are carried out by the customary methods; for example, the reaction products can be purified by chromatography on polar support materials such as silica gel or ®Sephadex LH 20 using solvents such as lower alkanols such as methanol or chloroform or ethyl acetate or methanol/chloroform mixtures, but also by extractive methods such as liquid/liquid extraction or solid/liquid extraction or by crystallization.

The derivatives of elaiophylin show anthelmintic action, in particular against Haemonchus, Trichostrongylus, Ostertagia, Cooperia, Chabertia, Strangyloides, Oesophagostromum, Hyostrongylus, Ancylostoma, Ascaris and Heterakis. The activity against gastrointestinal strongylidae and lung worms, which attack in particular, household and productive animals is particularly pronounced.

The elaiophylin derivatives can basically be administered as such in substance. Use mixed with suitable excipients is preferred. The customary feed mixtures can be used as excipients.

The invention is further illustrated in the attached examples. Percentage data relate to the weight and mixture proportions with liquids relate to the volume, unless stated otherwise.

The structural elucidation of the novel compounds was carried out by means of elemental analysis, infrared spectroscopy (IR), FAB mass spectrometry (NaCl or KCl matrix) and two-dimensional (2D) $^1H$ and $^{13}C$ nuclear magnetic resonance spectra.

EXAMPLE 1

(process a))

11,11'-Di-O-Methylelaiophylin (formula IV, $R^1=CH_2$)

20.0 g (19.5 mmol) of elaiophylin (formula IV, $R^1=H$) are suspended in 100 ml of anhydrous methanol and 600 mg of anhydrous iron(III) chloride are added. IF this mixture is stirred for about 2–5 minutes at 20° C., a homogeneous orange-yellow solution is initially obtained. After rubbing with a glass rod, the product crystallizes out spontaneously. The mother liquor yields further product fractions after concentrating and cooling.

Yield: 18.9 g (92%)

M.p.: 171° C.

Analysis for $C_{56}H_{92}O_{18}$ (1053.3):

C (calc.) 63.8% H (calc.) 8.8%:

C (found) 63.6% H (found) 8.7%.

EXAMPLE 2

(process b))

2,2',3,3',4,4',5,5'-Octahydro-11,11'-di-O-methylelaiophylin (formula IV, $R^1=CH_3$, macrodiolide ring hydrogenated)

10.0 g (9.5 mmol) of 11,11'-di-O-methylelaiophylin (from Example 1) are suspended in 100 ml of methanol and hydrogenated using 0.5 g of 10 percent palladium on carbon (Riedel-de-Haen) at normal pressure and room temperature until the calculated amount of hydrogen has been taken up. After filtering off the catalyst and concentrating the solution to dryness, the product is recrystallized from diisopropyl ether.

Yield: 9.78 g (97%)

M.p.: 114° C.

$[\alpha]_D^{20}-49.5°$ (c−1, CH$_3$OH)

C (calc.) 63.3% H (calc.) 9.5%:

C (found) 63.0% H (found) 9.7%.

The product can also be obtained directly from elaiophylin in one step if the reaction s carried out in anhydrous methanol using 10 percent palladium on carbon from Merck (yield 87%).

EXAMPLE 3

(process c)

11-O-Methyl-seco-elaiophylin methyl ester (formula I, R$^1$=CH$_3$, XR$^2$=OCH$_3$)

2.15 g (2.04 mmol) of 11,11'-di-O-methylelaiophylin (from Example 1) are dissolved at room temperature in 40 ml of a sodium methanolate solution. After 1.5 h, 5.35 g (100 mmol) of ammonium chloride are added in one portion with stirring and the mixture is concentrated to dryness on a rotary evaporator. The residue is stirred in ethyl acetate and the precipitated sodium chloride is removed by filtration. The oil remaining after distilling off the solvent is filtered through silicag gel using ethyl acetate. The product can be isolated as a colorless powder after concentrating by stirring with n-pentane.

Yield: 2.03 g (89%)

M.p.: −45° C.

$[\alpha]_D^{20}-45°$ (c−1, CH$_3$OH)

C (calc.) 62.3% H (calc.) 9.0%:

C (found) 62.1% H (found) 9.1%.

The compound can also be prepared directly from elaiophylin (formula IV, R$^1$=H) as follows:

2.10 g (2.04 mmol) of elaiophylin are suspended in 20 ml of anhydrous methanol and 60 mg of anhydrous iron(III) chloride are added. After stirring for 5 min at room temperature, 20 ml of a 2M sodium metahnolate solution are added and the procedure is then as described above.

Yield: 1.80 g (79%)

EXAMPLE 4

(process c)

2,3,4,5-Tetrahydro-11-O-methylsecoelaiophylin methyl ester (formula I, hydrogenated, R$^1$=CH$_3$, XR$^2$=OCH$_3$)

2.00 g (1.88 mmol) of 2,2',3,3',4,4',5,5'-octahydro-11,11'-di-O-methylaelaiophylin (from Example 2) are dissolved in 30 ml of a 2M sodium methanolate solution at room temperature. After 5 h, the reaction is complete according to the tin layer chromatogram (silica gel, dichloromethane/methanol 9/1, R$_f$=0.47). After addition of 5.35 g (100 mmol) of ammonium chloride and stirring for 5 min, the mixture is concentrated to dryness on a rotary evaporator and worked up analogously as described in Example 3. 656 mg (31%) of product of melting point 81° C. crystallize from diisopropyl ether.

FAB MS (KCl matrix) cluster ion (M+K)$^+$: m/e=601

Analysis for C$_{29}$H$_{54}$O$_{10}$ (562.74):

C (calc.) 61.9% H (calc.) 9.6%:

C (found) 61.7% H (found) 9.7%.

EXAMPLE 5

(process e)

2,3,4,5-Tetrahydro-11-O-methylsecoelaiophylin methyl ester (formula I, hydrogenated, R$^1$=CH$_3$, XR$^2$=OCH$_3$)

2.60 g (4.65 mmol) of 11-O-methylsecoelaiophylin methyl ester (product from Example 3) are dissolved in 50 ml of methanol and hydrogenated using 0.20 g of 10 percent palladium/carbon (Riedel-de-Haein) at normal pressure and room temperature until the calculated amount of hydrogen has been taken up. After filtering off the catalyst and concentrating, the residue is crystalized from diethyl ether/diisopropyl ether.

Yield: 1.62 g (62%)

Analytical data: see Example 4)

EXAMPLE 6

(process g)

2,3,4,5-Tetrahydro-11-O-methylsecoelaiophylincarboxamide (formula I, hydrogenated, R$^1$=CH$_3$, XR$^2$=OCH$_3$)

0.66 g (1.17 mmol) of 2,3,4,5-tetrahydro-11O-methylsecoelaiophylin ethyl ester (from Example 4 or 5) are dissolved in 50 ml of a solution of ammonia in methanol saturated at 0° C. and left for 48 h at room temperature in a closed reaction vessel. The reaction mixture is then concentrated to dryness and the residue is chromatographed on silica gel. Using ethyl acetate, 100 mg (15%) of unreacted starting compound are recovered. The product is eluted on addition of 10 percent methanol in ethyl acetate, and is isolated as a colorless solid after concentrating.

Yield: 0.51 g (79.5%)

IR (KBr) 1675 cmhu −1 (amide I), 1620 cm$^{-1}$ (amide II)

$[\alpha]_D^{20}-58.3°$ (c=1, CH$_3$OH)

C (calc.) 61.4% H (calc.) 9.7% N (calc.) 2.5%:

C (found) 61.3% H (found) 9.6% N (found) 2.3%.

EXAMPLE 7

(process h)

3',4',7-Tri-O-acetyl-11O-methylsecoelaiophylin methyl ester (formula I, R$^1$=CH$_3$, XR$^2$=OCH$_3$, R$^3$in the 3'-, 4'-and 7-position=COCH$_3$)

1.12 g (2.01 mmol) of 11-O-methylsecoelaiophylin methyl ester (from Example 3) are dissolved in 10 ml of dichloromethane, 10 ml of pyridine and 10 ml of acetic anhydride. The solution is allowed to stand for 14 h at room temperature and diluted with 200 ml of diethyl ether, and the organic phase is shaken with saturated aqueous sodium hydrogencarbonate solution unti lit has a neutral reaction. After drying over sodium sulfate, concentrating and filtering through silica gel with diisopropyl ether, the product is recrystallized from diisopropyl ether/n-pentane.

Yield: 0.65 g (45%)

M.p.: 165°−165° C.

IR (KBr) 1740 (acetate), 1725 (methyl ester), 1650/1620 (C=C)

$[\alpha]_D^{20}-21.2°$ (c−1, CH$_3$OH)

Characteristic $^{13}$C data (δ ppm in pyridine-d$^5$): 93.90 (C-1'), 170.91, 170.76, 170.03 (OAc), 167.25 (C-1), 103.86 (C-11)

Analysis for C$_{35}$H$_{56}$O$_{13}$ (684.8):
C (calc.) 61.4% H (calc.) 8.3%:
C (found) 61.7% H (found) 8.5%.

EXAMPLE 8

(process e)

3',4',7(or 9)-Tri-O-acetyl-11-O-methyl-2,3,4,5-tetrahydrosecoelaiophylin methyl ester (formula I, hydrogenated, R$^1$=CH$_3$, XR$^2$=OCH$_3$, R$^3$ in the 3'-,4'-,7-position COCH$_3$)

0.80 g (1.16 mmol) of 3',4',7(or 9)-tri-O-acetyl-11-O-methylsecoelaiophylin methyl ester (from Example 7) are dissolved in 15 ml of methanol and hydrogenated using 0.10 g of 10 percent palladium/carbon (Riedel-de-Haen) at normal pressure and room temperature until the calculated amount of hydrogen has been taken up. After filtering over corolite, concentrating and drying in vacuo 0.79 g (99%) of product are obtained as a colorless solid.

IR (KBr) 1740 (OAc), 1720 (methyl ester)
$[\alpha]_D^{20}$ −49° (c−1, CH$_3$OH)
FAB MS (KCl matrix) cluster ion (M+K)$^+$:m/e=727
Analysis for C$_{35}$H$_{60}$O$_{13}$ (688.85):
C (calc.) 61.0% H (calc.) 8.8%:
C (found) 61.4% H (found) 9.0%.
Characteristic $^{13}$C data (δ ppm in pyridine-d$^5$): 173.676 (C-1), 171.66, 170.79, 170.04 (OAc), 103.86 (C-11), 93.86 (C-1')

EXAMPLE 9

(process h)

The product described in Example 8 can also be prepared as follows:

0.56 g (1.00 mmol) of 2,3,4,5-tetrahydro-11O-methylsecoelaiophylin methyl ester (from Example 5) are dissolved in 2 ml of dichlormethane, 2 ml of pyridine and 2 ml of acetic anhydride. The solution is allowed to stand for 16 h at room temperature and worked up analogously as described in Example 7.

Yield: 0.48 g (69%)
Analytical data: see under Example 8

EXAMPLE 10

(process i)

3',4',7-Tri-O-acetylsecoelaiophylin methyl ester (formula I, R$^1$=H, XR$^2$=OCH$_3$, R$^3$ in the 3'-,4'-,7-position COCH$_3$)

1.37 g (2.00 mmol) of 3',4',7-tri-O-acetyl-11O-methylsecoelaiophylin methyl ester (from Example 7) are dissolved in 10 ml of isopropanol and 0.1 ml of water. 50 mg of copper(II) chloride are added and the mixture is stirred at room temperature until completion of the reaction (TLC checking on silica gel using dichloromethane/methanol 40:1) (reaction time about 15 min). After addition of 100 ml of ether, the organic phase is washed twice with 50 ml of sodium hydrogencarbonate solution each time, dried (Na$_2$SO$_4$) and concentrated. The product is crystallized from diisopropyl ether/n-pentane.

Yield: 0.79 g (58.9%)
M.p.: 147°-148° C. (dec.)
$[\alpha]_D^{20}$ −59° (c−1, CH$_3$OH)
FAB MS (KCl matrix) cluster ion (M+K)$^+$:m/e=709
Analysis for C$_{35}$H$_{54}$O$_{13}$ (670.8):
C (calc.) 60.9% H (calc.) 8.1%:
C (found) 61.2% H (found) 8.2%.
Characteristic $^{13}$C data (δ ppm in pyridine-d$^5$): 171.10, 170.81, 170.06, (OAc), 167.25 (C-1), 100.08 (C-11), 93.81 (C-1')

EXAMPLE 11

(process e)

3',4',7-Tri-O-acetyl-2,3,4,5-tetrahydrosecoelaiophylin methyl ester (formula I, hydrogenated, R$^1$=H, XR$^2$=OCH$_3$, R$^3$ in the 3'-,4'-,7-position COCH$_3$)

0.45 g (0.67 mmol) of product from Example 10 are dissolved in 10 ml of ethyl acetate and hydrogenated using 100 mg of 10 percent palladium/carbon (Riedel-de-Haen) at normal pressure and room temperature until the calculated amount of hydrogen has been taken up. After filtering off the catalyst and stripping off the solvent, the residue is crystallized from diisopropyl ether/n-pentane.

Yield: 0.36 g (79%)
M.p.: 112°-113° C.
Analysis for C$_{34}$H$_{58}$O$_{13}$ (674.8):
C (calc.) 60.5% H (calc.) 8.6%:
C (found) 60.3% H (found) 8.6%.
$^{13}$C NMR data (δ ppm in pyridine-d$^5$)

| | |
|---|---|
| 173.78 (C-1) | 48.90 (C-14) |
| 171.88, 170.84, 170.10 (OAc) | 43.11 (C-8) |
| 100.04 (C-11) | 38.93 (C-12) |
| 93.85 (C-1') | 38.29 (C-10) |
| 77.40 (C-7) | 34.99, 32.91 (C-2, C-3) |
| 70.93 (C-9) | 34.09 (C-6) |
| 70.82 (C-13) | 31.00 (C-2') |
| 70.34 (C-4') | 26.41, 25.52 (C-4, C-5) |
| 67.53 (C-3') | 20.86, 20.75, 20.56 (OAc) |
| 66.88 (C-15) | 19.77 (C-20) |
| 65.55 (C-5') | 19.51, 16.84, 15.73, 9.74 |
| 51.25 (CO$_2$CH$_3$) | 9.11, 7.46 (CH$_3$) |

EXAMPLE 12

(process h)

3',4',7(or 9)-Tri-O-benzyl-11-O-methylsecoelaiophylin methyl ester (formula I, R$^1$=CH$_3$, XR$^2$=OCH$_3$, R$^3$ in the 3'-,4'-,7-position COCH$_3$)

1.08 g (1.93 mmol) of 11-O-methylsecoelaiophylin methyl ester (from Example 3), 2.26 g (10.0 mmol) of benzoic anhydride and 300 mg (2.45 mmol) of 4-dimethylaminopyridine are dissolved in 15 ml of dichloromethane and 15 ml of pyridine. After 5 h at room temperature, 3 ml of anhydrous methanol are added and the mixture is worked up after 10 min as follows: after diluting with 150 ml of diethyl ether, the organic phase is washed 3 times with 50 ml of a saturated aqueous sodium hydrogencarbonate solution each time, dried (Na$_2$SO$_4$) and concentrated. The residue is chromatographed on silica gel using ethyl acetate/hexane (¼). The product is a colorless solid.

Yield: 0.85 g (50.5%)
$[\alpha]_D^{20}$ −37° (c−1, CH$_3$OH)

C (calc.) 68.9% H (calc.) 7.1%:
C (found) 68.6% H (found) 7.1%.
IR (KBr) 1690 (methyl ester); 1725 (benzoate)

EXAMPLE 13

(process e)

7,11-Anhydro-2,3,4,5-tetrahydrosecoelaiophylin methyl ester (formula III, $XR^2=OCH_3$, $R^3=H$)

1.25 g (2.23 mmol) of 11-O-methylsecoelaiophylin methyl ester (from Example 3) are dissolved in 50 ml of anhydrous methanol and hydrogenated using 300 mg of 10 percent palladium/carbon (Merck) at room temperature and normal pressure until the calculated amount of hydrogen has been taken up. The reaction solution is concentrated and the residue is chromatographed on 200 g of silica gel using ethyl acetate/hexane (2/1). The stereoisomer products indicated in the following by (A) and (B) are smoothly separated in this case and obtained as colorless oils in a total yield of 82%.

Product (A)

Yield: 0.55 g (47%)

$R_f$ value: 0.30 (on silica gel using $CH_2Cl_2/CH_3OH$ 15/1)
$[\alpha]_D^{20} -119°$ (c-1, $CH_3OH$)
IR ($CH_2Cl_2$) 1690 cm$^{-1}$ (methyl ester);
Analysis for $C_{28}H_{50}O_9$ (530.69):
C (calc.) 63.3% H (calc.) 9.5%:
C (found) 63.0% H (found) 9.4%.
FAB MS (NaCl matrix) cluster ion $(M+Na)^+$
m/e=553
Selected $^{13}C$ data ($\delta$, ppm in pyridine-d$^5$)
173.95 (C-1), 100.74 (C-11), 94.56 (C-1'),
51.18 (ester-$CH_3$)

Product (B)

Yield: 0.41 g (35%)

$R_f$ value: 0.19 (on kieselguhr with $CH_1Cl_2/CH_3OH$ 15/1
$[\alpha]_D^{20} -87°$ (c-1, $CH_3OH$)
IR ($CH_2Cl_2$) 1720 cm$^{-1}$ (methyl ester);
Analysis for $C_{28}H_{50}O_9$ (530.69):
C (calc.) 63.3% H (calc.) 9.5%:
C (found) 63.1% H (found) 9.6%.
FAB MS (NaCl matrix) cluster ion $(M+Na)^+$
m/e=553
Selected $^{13}C$ data ($\delta$, ppm in pyridine-d$^5$)
173.82 (C-1), 102.03 (C-11), 94.34 (C-1'),
51.18 (ester-$CH_3$)
The product from Example 4 is not detectable by tin layer chromatography.

EXAMPLE 14

(process h)

7,11-Anhydro-3',4'9-tri-O-acetyl-2,3,4,5-tetrahydrosecoelaiophylin methyl ester, stereoisomer (A) (formula III, $XR^2=OCH_3$, $R^3=COCH_3$)

1.10 g (2.07 mmol) of 7,11-anhydro-2,3,4,5-tetrahydrosecoelaiophylin methyl ester (stereoisomer A from Example 13) are acetylated for 40 h at room temperature in 7 ml of dichloromethane, 7 ml of pyridine and 7 ml of acetic anhydride. After diluting with 200 ml of diethyl ether, the organic phase is washed with saturated aqueous sodium hydrogencarbonate solution utnil it has a neutral reaction. Drying ($Na_2SO_4$), concentrating and column filtration through silica gel using diisopropyl ether/hexane (1/1) yields the product as a colorless, viscous oil.

Yield: 1.20 g (88%)
$[\alpha]_D^{20} -133°$ (c-1, $CH_3OH$)
FAB MS (NaCl matrix) cluster ion $(M+Na)^+$
m/e=695
Analysis for $C_{34}H_{56}O_{12}$ (656.81):
C (calc.) 62.1% H (calc.) 8.6%:
C (found) 61.9% H (found) 8.4%.
Selected $^{13}C$ data ($\delta$, ppm in pyridine-d$^5$)
173.90 (C-1), 170.79, 170.34, 169.94 (OAc), 100.53 (C-11), 94.42 (C-1'), 51.24 (ester-$CH_3$)

EXAMPLE 15

(process h)

7,11-Anhydro-3',4',9-tri-O-acetyl-2,3,4,5-tetrahydrosecoelaiophylin methyl ester, stereoisomer (B)

(formula III, $XR^2=OCH_3$, $R^3=COCH_3$)

0.70 g (1.32 mmol) of 7,11-anhydro-2,3,4,5-tetrahydrosecoelaiophylin methyl ester (stereoisomer B from Example 13) are acetylated for 40 h at room temperature in 5 ml of dichloromethane, 5 ml of pyridine and 5 ml of acetic anhydride. The isolation of the product is carried out entirely analogously as described in Example 14.

Yield: 0.85 g (98%) as a colorless solid
FAB MS (KCl matrix) cluster ion $(M+Na)^+$
m/e=695
Analysis for $C_{34}H_{56}O_{12}$ (656.81):
C (calc.) 62.1% H (calc.) 8.6%:
C (found) 61.9% H (found) 8.3%.
Selected $^{13}C$ data ($\delta$, ppm in pyridine-d$^5$)
173.76 (C-1), 170.77, 170.34, 170.10 (OAc), 101.80 (C-11), 94.04 (C-1'), 51.25 (ester-$CH_3$)

EXAMPLE 16

(process d)

Preparation of the products A and B of Example 13 by process d)

563 mg (1.00 mmol) of 2,3,4,5-tetrahydro-11O-methylsecoelaiophylin methyl ester (formula I, hydrogenated, $R^1=CH_3$, $XR^2=OCH_3$) from Example 4 or from Example 5 are dissolved in 5 ml of methanol (anhydrous) and 10 mg of $FeCl_3$ are added at room temperature. After 10 min, the mixture is concentrated and the product is separated as described in Example 13.

Yield of product A: 239 mg (45%)
Yield of product B: 212 mg (40%)
For analytical data see under Example 13.

EXAMPLE 17

(process d)

7,11-Anhydrosecoelaiophylin methyl ester (formula III, $XR^2=OCH_3$, $R^3=H$)

0.95 g (1.70 mmol) of 11-O-methylsecoelaiophylin methyl ester from Example 3 are dissolved at 20° C. in 10 ml of anhydrous methanol and 30 mg of $FeCl_3$ are added. AFter 10 min, the mixture is concentrated and chromatographed on 50 g of silica gel using ethyl acetate/hexane (2/1). The C-11 epimeric products A and B are smoothly separated in each case and are isolated as colorless solids after drying in a high vacuum.

C-11-Epimer (A):

Yield: 0.44 g (49%)
$R_f$ value: 0.30 (on silica gel using ethyl acetate
$[\alpha]_D^{20} -134°$ (c−1, CH$_3$OH)
IR (KBr) 1715 (c=O), 1640, 1620 cm$^{-1}$ (C=C)
FAB MS (NaCl matrix) cluster ion (M+Na)$^+$ m/e=549
Analysis for C$_{28}$H$_{46}$O$_9$ (526.66):
C (calc.) 63.8% H (calc.) 8.8%:
C (found) 63.5% H (found) 8.7%.

C-11-Epimer (B):

Yield: 0.38 g (42%)
$R_f$ value: 0.16 (on silica gel using ethyl acetate
$[\alpha]_D^{20} -58.2°$ (c−1, CH$_3$OH)
IR (KBr) 1715 (c=O), 1640,
FAB MS (NaCl matrix) cluster ion (M +Na)$^+$ m/e=549
Analysis for C$_{28}$H$_{46}$O$_9$ (526.66):
C (calc.) 63.8% H (calc.) 8.8%:
C (found) 63.6% H (found) 8.8%.

EXAMPLE 18

(process a) and c))

11-O-(2-Phenylethyl)secoelaiophylin methyl ester
(formula I, R$^1$=CH$_2$CH$_2$C$_6$H$_5$, XR$^2$=OCH$_3$)

2.00 g (1.95 mmol) of elaiophylin (formula IV, R$^1$=H) are suspended in a solution of 3.00 g (24.6 mmol) of 2-phenylethanol in 17 ml of dichloromethane and 100 mg of iron(III) chloride are added. After stirring for about 5 min. at 20° C., a homogeneous solution is obtained and the starting compound has reacted quantitatively (TLC checking: dichloromethane/methanol 9/1). 40 ml of a 1M sodium methanolate solution are then added and the mixture is stirred for 1.5 h at room temperature. After 1.5 hr, 5.35 g (100 mmol) of ammonium chloride are added and the mixture is concentrated to dryness on a rotary evaporator. Further working up is carried out analogously as described in Example 3.
Yield: 0.94 g (37%)
Analysis for C$_{36}$H$_{56}$O$_{10}$ (648.83):
C (calc.) 66.6% H (calc.) 8.69%:
C (found) 66.4% H (found) 8.72%.

EXAMPLE 19

(process (a) and (b)

11-O-Propylsecoelaiophylin methyl ester (formula I, R$^1$=CH$_7$, XR$^2$=OCH$_3$)

2.00 g (1.95 mmol) of elaiophylin (formula IV, R$^1$=H) are suspended in a solution of 1.2 g (20 mmol) of n-propanol in 18 ml of dichloromethane and 100 mg of anhydrous iron(III) chloride are added. After stirring for about 5 min. at 20° C., a homogeneous solution is obtained (TLC checking: analogously to Example 16). AFter addition of 40 ml of a 1M sodium methanolate solution and stirring for 1.5 hours at room temperature, 5.35 g (100 ml) of ammonium chloride are added and the product is isolated analogously as described in Example 3.
Yield: 1.20 g (52%)
Analysis for C$_{31}$H$_{54}$O$_{10}$ (586.76):
C (calc.) 63.4% H (calc.) 9.2%:
C (found) 63.1% H (found) 9.0%.
IR (CHCl$_3$) 1695 cm$^{-1}$ (ester)

Anthelmintic action of the elaiophylin derivatives

The anthelmintic action of the elaiophylin derivatives was investigated in lambs of 30 to 40 kg body weight. For this purpose, the lambs were infected artificially with infectious stages of abomasal nematodes (*Haemonchus contortus*). Administration of the elaiophylin derivatives was carried out after conclusion of the development time (prepatency period) of the nematodes.

The percentage reduction of the sheep nematodes was determined by means of coproscoic investigations before and up to 14 days after the administration of the elaiophylin derivatives and subsequent section using helminthological working up (see Table 1). Elaiophylin was used as a comparison substance. The antibacterial activity of the elaiophylin derivatives according to the invention against *Staph. aureus* and *Stept. pyrogenes* was additionally also determined. Surprisingly, the compounds according to the invention show no or only very low antibacterial activity. The compounds according to the invention are therefore useful directly, in particular for use as anthelmintics, since here an antibacterial effect is undesired.

TABLE 1

| Administered compound from Example | Dosage (mg/kg) | Reduction of. *H. contortus* (%) | Antibacterial activity (μg/ml) against | |
|---|---|---|---|---|
| | | | *Staph. aureus* | *Strep. pyrogenes* |
| Elaiopylin | 2.5 (s.c.) | 35–45 | 1.56 | 1.56 |
| | 5.0 (oral) | 70–95 | | |
| 3 | 2.5 (s.c.) | — | >100 | >100 |
| | 5.0 (oral) | 70–90 | | |
| 4 | 2.5 (s.c.) | 50–70 | >100 | >100 |
| | 5.0 (oral) | 30–40 | | |
| 7 | 2.5 (s.c.) | 40–75 | >100 | >100 |
| | 5.0 (oral) | 50–70 | | |
| 10 | 2.5 (s.c.) | 30–70 | >100 | >100 |
| | 5.0 (oral) | — | | |
| 17 | 2.5 (s.c.) | — | >100 | >100 |
| | 5.0 (oral) | 30–40 | | |

We claim:
1. An elaiophylin derivative of the formulae (III)

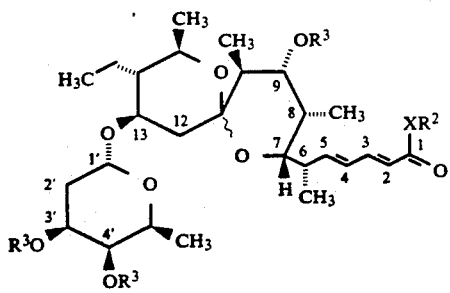

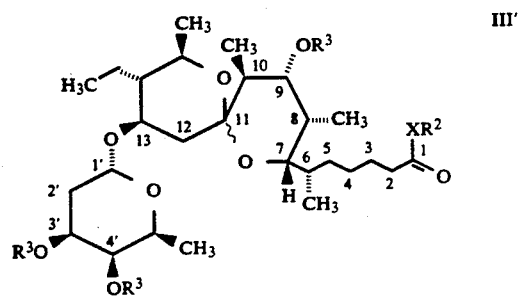

in which the C=C double bonds in he 2,3 and 4,5 position may also be hydrogenated to form formula (III') and in which X is O or, if the C=C double bonds in formula (III) are hydrogenated in the 2,3 and 4,5 position, is also NH, $R^2$ is hydrogen or $C_1$-$C_4$-alkyl or, if X is NH, is a radical having the formula (VI)

$$-(CH_2)_n-R^4 \qquad (VI)$$

in which
n = 1 to 3 and
$R^4$ is hydrogen, $C_1$-$C_6$-alkyl, phenyl or naphthyl, thiophene, furan, pyridine, pyrimidine or pyrazine, and
$R^3$ is hydrogen or a radical of the formula (II)

$$-C-(CH_2)_n-R^4 \qquad (II)$$

in which n and $R^4$ have the abovementioned meanings.

2. An elaiophylin derivative of the formula (III) as claimed in claim 1 in which
$R^4$ is hydrogen, $C_1$-$C_4$-alkyl or phenyl.

3. An elaiophylin derivative as claimed in claim 1 for use as a pharmaceutical.

4. An elaiphylin derivative as claimed in claim 1 for use as an anthelmintic.

5. A pharmaceutical composition having anthelmintic action containing an anthelmintically effective amount of one or more different compounds of the formula (III) as claimed in claim 1 together with a pharmaceutically acceptable carrier.

* * * * *

UNITED STATES PATENT AND TRADEMARK OFFICE
CERTIFICATE OF CORRECTION

PATENT NO. : 5,096,905
DATED : March 17, 1992
INVENTOR(S) : Gerhard Kretzschmar et al.

It is certified that error appears in the above-identified patent and that said Letters Patent is hereby corrected as shown below:

Item [75]
Title Page, Inventors, change "Keikheim" to --Kelkheim--.

Claim 1, column 19, line 1, change "he" to --the--.

Claim 4, column 20, line 11, change "elaiphylin" to --elaiophylin--.

Signed and Sealed this

Twenty-eighth Day of September, 1993

Attest:

BRUCE LEHMAN

Attesting Officer     Commissioner of Patents and Trademarks